United States Patent [19]

Müller-Lierheim

[11] Patent Number: 4,828,563
[45] Date of Patent: May 9, 1989

[54] IMPLANT

[75] Inventor: Wolfgang G. K. Müller-Lierheim, Gräelfing, Fed. Rep. of Germany

[73] Assignee: Dr. Muller-Lierheim AG, Planegg, Fed. Rep. of Germany

[21] Appl. No.: 85,228

[22] Filed: Aug. 13, 1987

Related U.S. Application Data

[63] Continuation of Ser. No. 875,546, Jun. 18, 1986, abandoned.

[30] Foreign Application Priority Data

Jun. 18, 1985 [DE] Fed. Rep. of Germany ....... 3521684

[51] Int. Cl.$^4$ .................. A61F 2/28; A61K 39/00; A61K 1/02
[52] U.S. Cl. ........................................ 623/16; 623/66; 427/2; 424/422; 424/423
[58] Field of Search ............ 623/11, 15, 16, 22, 623/23; 521/56, 149; 525/61; 526/201; 128/1 R, 155, 156; 424/85, 422, 423; 530/387, 389, 390, 391; 427/2

[56] References Cited

U.S. PATENT DOCUMENTS

| | | | |
|---|---|---|---|
| 3,983,000 | 9/1976 | Messing et al. | 530/391 X |
| 4,071,409 | 1/1978 | Messing et al. | 530/391 X |
| 4,164,794 | 8/1979 | Spector et al | 623/23 X |
| 4,451,568 | 5/1984 | Schneider et al. | 428/420 X |
| 4,458,678 | 7/1984 | Yannas et al. | 623/15 X |
| 4,505,266 | 3/1985 | Yannas et al. | 623/11 X |
| 4,542,069 | 9/1985 | Maüz et al. | 526/201 X |
| 4,565,784 | 1/1986 | Franzblau et al. | 435/240 |
| 4,568,706 | 2/1986 | Noetzel et al. | 521/56 X |
| 4,598,122 | 7/1986 | Goldenberg | 525/61 |
| 4,608,052 | 8/1986 | Van Kamper et al. | 623/22 |

FOREIGN PATENT DOCUMENTS 3519073  12/1985  Fed. Rep. of Germany .

OTHER PUBLICATIONS

Takaoka et al., "Purification of a Bone-Inducing Substance (Osteogenic Factor) from a Murine Osteosarcoma", Biomedical Research, 2 (5), pp. 446-471 (1981).
Urist et al., "Bone Morphogenetic Protein", J. Dent. Res. Supplement to No. 6, vol. 50, pp. 1392-1406 (1971).
Weetall, "Tragergebundene Enzyme und ihre Anwendung in der Nahrungsmittel-und Getrankeindustrie" Chemiker-Zeitung, pp. 611-619 (1973).
Mittelmeier, et al., "Klinische Erfahrungen mit Collagen-Apatit-Implantation Zur lokalen Knochenregeneration", Z. Orthop. 121, pp. 115-123 (1983).

Primary Examiner—Richard J. Apley
Assistant Examiner—Alan W. Cannon
Attorney, Agent, or Firm—Fleit, Jacobson, Cohn & Price

[57] ABSTRACT

An implant having a surface coating of growth factors for animal or human cells, wherein the growth factors are covalently bonded to bonding-active groups of a polymer on the base body of the implant.

15 Claims, 1 Drawing Sheet

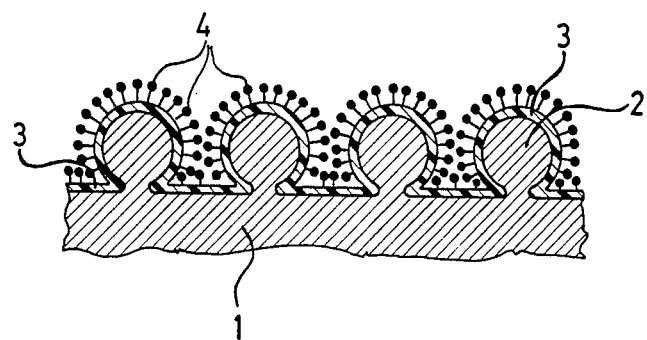

IMPLANT

This application is a continuation-in-part of application Ser. No. 875,546, filed June 18, 1986, now abandoned.

BACKGROUND OF THE INVENTION

The invention relates generally to an implant. In this specification, the term implant is used to denote not only prostheses but also artificial organs, for example artificial kidneys, vessels, skin substitute, artificial eye lenses, so-called intraocular lenses, dental prostheses and also contact lenses. In this specification also any reference to animal cells is intended to embrace human cells.

Biocompatibility and mechanical strength are essential requirements in respect of an implant material. There are various implant materials which tend to trigger off different reactions in the tissue around them. Thus for example metals such as copper, cobalt, nickel or vanadium exhibit toxic reactions. Compatible implant materials on a Co- or PMMA-base exhibit connective-tissue decapsulation and distancosteogenesis. Although vital implant materials such as Ti-alloys and $Al_2O_3$ ceramic do not exhibit any reaction, there is however a rejection effect caused by the biomechanism. It is to be expected of bioactive materials that they will produce a positive reaction in the body. On the one hand, they should promote or accelerate bone growth, while on the other hand there should be a true bond between the bone and the implant. That bond should be capable of transmitting not only compression forces but also shearing and tensile forces.

SUMMARY OF THE INVENTION

An object of the present invention is to provide an implant which enjoys enhanced biocompatibility and mechanical strength.

Another object of the invention is to provide a biocompatible and mechanically strong implant which affords a true bond between bone and implant.

Still another object of the present invention is to provide an implant adapted to permit therapeutic use of plastic materials.

Still a further object of the present invention is to provide an implant which enjoys biocompatibility and mechanical strength while also being resistant to corrosion of the base body thereof.

In accordance with the principles of the present invention, these and other objects are attained by an implant comprising a base body having a surface coating of a bioactive material thereon. The bioactive material includes a growth factor for animal cells (which as noted above also includes human cells), being covalently bonded to the surface of a polymer layer present on the implant base body. Said surface has bonding-active groups.

The above-mentioned coating with growth factors and possibly animal cells provides for enhanced compatibility of the implant. It is also possible to produce corneal implants with epithelial or endothelial cell coating. A high degree of biocompatibility is achieved and the implant is guaranteed to grow into position. The implant of the invention also permits therapeutic use of plastic materials, for example in the form of extracorporeal or implantable artificial organs and vessels. In the event of the implant having a metal base body, the polymer layer which is provided on the surface thereof also gives protection, in particular from corrosion thereof.

The growth factors used in the present invention may be metabolism products of human or animal cells. Blood serum or constituents thereof, in particular fibronectin, are also suitable as growth factors. It is also possible for the growth factor used to comprise a combination of cell metabolism products and biochemically modified natural products. Further suitable forms of growth factor are proteins which result in cell differentiation. That may involve proteins with active bone induction bone morphogenetic protein (J. Dent. Res. (1971), pages 1392–1406) which occur in the form of a bone past (bone substance-inducing proteins combined with for example, collagen). In that respect the growth factors may be in the form of bone powder extract. The bone powder extract may be bonded to the polymer surface with an extracellular matrix, which may be collagen-bearing. Also, monoclonal or polyclonal antibodies may be bonded to the polymer surface, which are directed against bone substance-inducing proteins and/or the extracellular matrix present in the environment of the human body in the vicinity of the implant. Also suitable is a collagen-apatite mixed preparation (Z. Orthop. 121 (1983), pages 115 to 123), in which the collagen is covalently bonded to the polymer surface.

For the utilization of monoclonal antibodies, the standard hybridoma technique for producing such antibodies is as follows: BALB/c mice were immunized by intraperitoneal injections of bone morphogenetic proteins emulsified in Freund's complete adjuvant (50 $\mu$g Protein). In periodical distances of 4 weeks 4 to 5 additional immunizations follow whereby each second immunization was conducted with 50 $\mu$g Protein emulsified in an incomplete Freund's adjuvant and the others with 50 $\mu$g Protein emulsified in a sodium chloride solution buffered with phosphate. Three days prior to fusion, mice demonstrating a sufficient titer (ELISA: $\leq 1:10,000$) were prepared by an intravenous Booster injection.

The spleen cells from the immunized mice and myeloma cells (P3X63-Ag.8.653, ATCC CRL 1580) were combined with a 5:1 ratio in DMEM (Dulbecco's Modified Eagle's Medium) and centrifugated. The cell pellet is mixed with polyethlene glycol in HEPE (4-(2-hydroxyethyl)-1-piperazinethan sulfon acid) buffer within 2 min. at 40° C. Then the mixture was diluted (pH was adjusted to 8.35) and centrifugated. The fusion products were aliquoted into 24-well microtiter culture plates and the plates were incubated for 10 to 14 days. Following positive identification by ELISA, hybrid cells were cloned.

These antibodies are immobilized at the prosthetic device. If the prosthetic device is implanted in the human body the antibodies can absorb at their N-terminal ends the bone-substance-inducing proteins from the environment in the human body.

The polymer surface may have oxirane groups as the bonding-active groups, for bonding the growth factor to the polymer surface. Other mechanisms for covalent bonding are disclosed in the journal 'Chemikerzeitung', 97th edition (1973), No 11, page 612. The polymer may be a copolymer which may be formed from at least two of the monomers consisting of methacrylamide, N-methylene-bis-methacrylamide, allylglycidylether or glycidylmethacrylate. The base body to which the polymer layer is applied may comprise metal or suitable plastic material, depending on the situation of use. One or more projections may be provided on the base body, to provide an improved anchoring effect. The one or more anchoring projections are preferably of such a configuration as to provide an undercut shape thereon, thereby further to enhance the anchoring action.

Further objects, features and advantages of the present invention will become apparent from the following description.

BRIEF DESCRIPTION OF THE DRAWING

The accompanying single figure of the drawing shows a sectional view of part of a surface of an implant according to the invention.

DESCRIPTION OF THE PREFERRED EMBODIMENT

Referring to the drawing which shows a part of an implant which may be for example in the form of a hip joint implant, the implant comprises a base body 1 which comprises for example metal. Provided on the surface of the implant are growth factors for animal cells which, as indicated above, therefore also embraces human cells.

The base body 1 of the implant comprises a plurality of anchoring projections 2 which serve to give an improved anchoring effect and also to increase the area of the surface of the implant. The projections 2 may be for example in the form of ball portions which are sintered on to the base body 1. The projections may also be of a different form, in which respect it is advantageous for them to be of such a configuration as to define undercut portions, as can be seen in the drawing. The undercut configurations ensure a strong anchoring effect in respect of the polymer layer and also the cells by way of which the implant is to be connected to the surrounding tissue.

Applied to the surface of the base body 1 and the anchoring projections 2 is a polymer layer which is indicated at 3 and the surface of which has bonding-active groups for covalent bonding of growth factors indicated at 4. The bonding-active groups are preferably oxirane groups. The growth factors which are thus bonded to the surface of the polymer coating by covalent bonding are selected depending on the purpose of use of the implant. If the implant is one that is intended to replace a bone or part thereof, for example for a hip joint, then the growth factors used are bone substance-inducing proteins (J. Dent. Res. 50 (1971), pages 1392 to 1406). Just traces of that protein are sufficient to stimulate mesenchymal cells for differentiation to give bone-forming cells.

A suitable polymer for the carrier surface is a copolymer which is formed from at least two of the monomers consisting of methacrylamide, N-methylene-bis-methacrylamide, allylglycidyl-ether or glycidylmethacrylate.

Reference will now be made to examples in respect of the immobilisation of proteins.

EXAMPLE 1

Carrier surfaces carrying amino groups may be activated for example with thiophosgene. An isothiocyanate is produced in that case on the carrier, as the activating species. The routines involved are shown below.

(a) Carrier activation

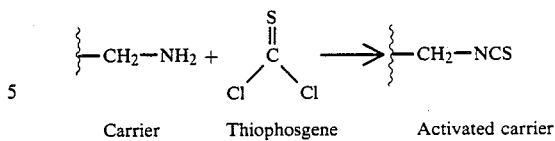

(b) Protein immobilisation

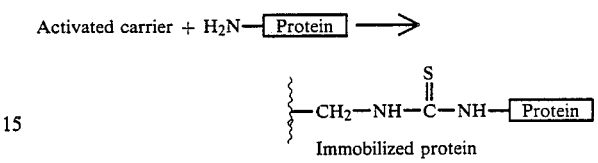

EXAMPLE 2

A wide reaction spectrum is afforded by the epichlorhydrin method. Therein, the carrier surface is spiked by means of epichlorhydrin with oxirane group-bearing spacers. The epoxy groups which are under ring tension may be opened under very mild reaction conditions mucleophilically with thiol, hydroxyl or amino groups.

(a) Carrier activation

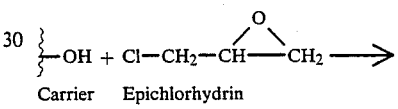

(b) Protein immobilisation

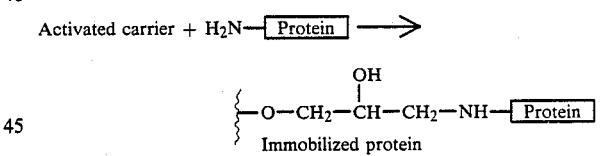

EXAMPLE 3

The effectiveness of an immobilisation action depends not only on the choice of the linking method but also the carrier-protein spacing.

Such aspects are taken into consideration for example by the bisepoxyoxirane method. In that method, one oxirane group is used for anchoring to the carrier and the second is used for fixing the protein.

(a) Carrier activation

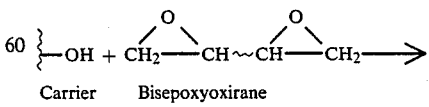

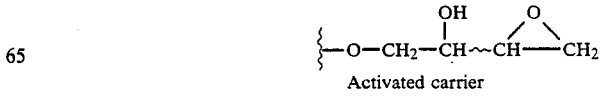

(b) Protein immobilisation

Activated carrier + H$_2$N—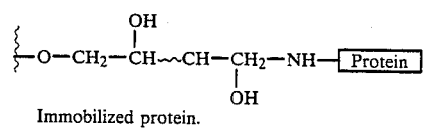

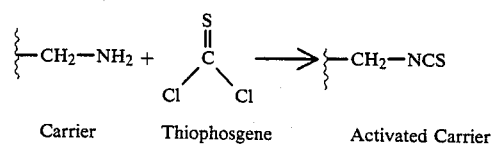

Immobilized protein.

Appropriate methods for the bonding of the antibody on the carrier surface are shown in the following examples.

EXAMPLE 4

Carrier surfaces carrying amino groups may be activated for example with thiophosgene. An isothiocyanate is produced in that case on the carrier, as the activating species. The routines involved are shown below.

(a) Carrier Activation

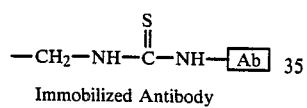

(b) Antibody Immobilization

Activated Carrier + H$_2$N—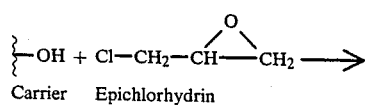 →

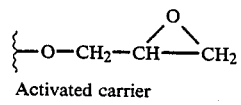

Immobilized Antibody

EXAMPLE 5

A wide reaction spectrum is afforded by the epichlorhydrin method. Therein, the carrier surface is spiked by means of epichlorhydrin with oxirane group-bearing spacers. The epoxy groups, which are under ring tension, may be opened under very mild reaction conditions nucleophillically with thiol, hydroxyl, or amino groups.

(a) Carrier Activation

}—OH + Cl—CH$_2$—CH——CH$_2$ →

Carrier  Epichlorhydrin

}—O—CH$_2$—CH——CH$_2$

Activated carrier (b) Antibody Immobilization

Activated Carrier + H$_2$N—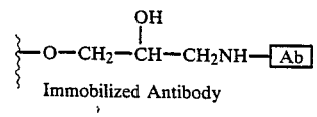 →

}—O—CH$_2$—CH—CH$_2$NH—[Ab]
         |
         OH

Immobilized Antibody

EXAMPLE 6

The effectiveness of an immobilization action depends not only on the choice of the linking method but also the carrier-protein spacing.

Such aspects are taken into consideration, for example, by the biepoxyoxirane method. In that method, one oxirane group is used for anchoring to the carrier and the second is used for fixing the protein.

(a) Carrier Activation

}—OH + CH$_2$——CH~CH——CH$_2$ →

Carrier  Bisepoxyoxirane

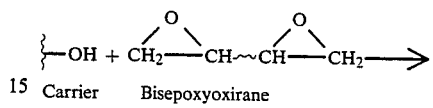

Activated Carrier (b) Antibody Immobilization

Activated Carrier + H$_2$N—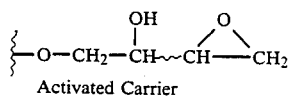 →

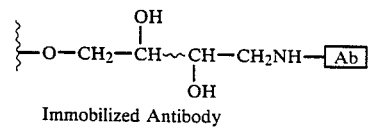

Immobilized Antibody

I claim:

1. An implant comprising:
a rigid, implantable base body;
a polymer layer anchored to the surface of said base body, said polymer layer having bonding-active groups at least on a polymer surface thereof remote from said base body
polyclonal antibodies bonded to said polymer surface by said bonding-active groups; and
growth factors for animal cells including bone substance-inducing proteins bound to said polyclonal antibodies, wherein said polyclonal antibodies are receptors for said bone substance-inducing proteins.

2. An implant as set forth in claim 1 wherein said growth factors are animal cell metabolism products.

3. An implant as set forth in claim 1 wherein said growth factors include blood serum.

4. An implant as set forth in claim 1 wherein said growth factors include at least one blood serum constituent.

5. An implant as set forth in claim 3 wherein said growth factors include fibronectin.

6. An implant as set forth in claim 1 wherein said growth factors include a combination of cell metabolism product and biochemically modified natural product.

7. An implant as set forth in claim 1 wherein said growth factors include protein leading to cell differentiation.

8. An implant as set forth in claim 7 wherein said growth factors are in the form of bone powder extract.

9. An implant as set forth in claim 8 wherein said bone powder extract is bonded with an extracellular matrix to said polymer surface.

10. An implant as set forth in claim 1 wherein said polymer surface has oxirane groups.

11. An implant as set forth in claim 1 wherein said polymer is a copolymer comprising at least two monomers selected from the group consisting of methacrylate, N-methylene-bis-methacrylamide, allylglycidyl ether and glycidylmethacrylate.

12. An implant as set forth in claim 1 wherein said base body comprises metal.

13. An implant as set forth in claim 1 wherein said base body has anchoring means thereon.

14. An implant as set forth in claim 13 wherein said anchoring means comprise projections forming undercut configurations at the surface of said base body.

15. A bone implant comprising:
a rigid, implantable base body;
a polymer layer anchored to the surface of said base body, said polymer layer having bonding-active groups on a polymer surface remote from said base body; and
polyclonal antibodies bonded to said polymer surface by said bonding-active groups, said polyclonal antibodies being receptor for bone substance-inducing proteins;
wherein, upon implantation of said bone implant in an animal or human body, said polyclonal antibodies absorb bone substance-inducing proteins from the environment in the body.

* * * * *